(12) United States Patent
Kiyota

(10) Patent No.: US 8,159,675 B2
(45) Date of Patent: Apr. 17, 2012

(54) OBSERVATION DEVICE AND WAVELENGTH LIMITING FILTER

(75) Inventor: Yasujiro Kiyota, Tokyo (JP)

(73) Assignee: Nikon Corporation, Tokyo (JP)

( * ) Notice: Subject to any disclaimer, the term of this patent is extended or adjusted under 35 U.S.C. 154(b) by 128 days.

(21) Appl. No.: 12/461,013

(22) Filed: Jul. 29, 2009

(65) Prior Publication Data

US 2009/0296208 A1 Dec. 3, 2009

Related U.S. Application Data

(63) Continuation of application No. PCT/JP2008/000593, filed on Mar. 14, 2008.

(30) Foreign Application Priority Data

Mar. 19, 2007 (JP) ................................. 2007-071099

(51) Int. Cl.
*G01J 3/51* (2006.01)
*G02B 21/00* (2006.01)

(52) U.S. Cl. ...................... 356/416; 435/288.7; 435/808

(58) Field of Classification Search ............... 435/288.7; 382/133
See application file for complete search history.

(56) References Cited

U.S. PATENT DOCUMENTS

| | | |
|---|---|---|
| 3,180,216 A | 4/1965 | Osterberg |
| 4,972,258 A | 11/1990 | Wolf et al. |
| 5,022,744 A | 6/1991 | Leiter |
| 5,510,246 A * | 4/1996 | Morgan .......................... 435/39 |
| 6,437,913 B1 | 8/2002 | Kishi |
| 2005/0168808 A1 | 8/2005 | Ishiwata |

FOREIGN PATENT DOCUMENTS

| | | |
|---|---|---|
| DE | 36 06 755 A1 | 11/1986 |
| DE | 101 32 360 C1 | 11/2002 |
| GB | 821378 | 10/1959 |
| JP | A 5-297280 | 11/1993 |
| JP | A 11-84260 | 3/1999 |
| JP | A 2000-330029 | 11/2000 |
| JP | A 2004-85833 | 3/2004 |
| JP | A 2007-6852 | 1/2007 |
| WO | WO 93/13444 | 7/1993 |

OTHER PUBLICATIONS

European Search Report issued in corresponding European Patent Application No. 08720479.8, mailed May 21, 2010.

* cited by examiner

*Primary Examiner* — F. L. Evans
(74) *Attorney, Agent, or Firm* — Oliff & Berridge, PLC

(57) ABSTRACT

An observation device observing a sample cultured in a culture vessel includes an illuminating unit including an illumination optical system and illuminating the sample, an image-capturing unit including an imaging sensor and generating an image by capturing an image of the sample illuminated by the illuminating unit, and a wavelength limiting filter being placed on an optical axis of the illumination optical system and between the illuminating unit and the image-capturing unit, and limiting a part of wavelengths of an illumination light from the illumination optical system in accordance with optical absorption properties of an additive contained in a culture medium used for culturing the sample. Accordingly, it is possible to suppress a change of the image resulting from the additive and to enable to generate an appropriate image in an automatic observation.

11 Claims, 11 Drawing Sheets

OBSERVATION DEVICE AND WAVELENGTH LIMITING FILTER

CROSS REFERENCE TO THE RELATED APPLICATIONS

This application is a continuation application of International Application PCT/JP2008/000593, filed Mar. 14, 2008, designating the U.S., and claims the benefit of priority from Japanese Patent Application No. 2007-071099, filed on Mar. 19, 2007, the entire contents of which are incorporated herein by reference.

BACKGROUND

1. Field

The present application relates to an observation device observing a sample cultured in a culture vessel, and a wavelength limiting filter for the observation device.

2. Description of the Related Art

Conventionally, a phase-contrast microscope or the like is known as an observation device observing a sample cultured in a culture vessel (for example, refer to Patent Document 1: Japanese Unexamined Patent Application Publication No. H11-84260). There are various microorganisms, cells, and so on as the samples observed by the observation device as stated above.

Incidentally, it is often the case that an additive such as a pH indicator is added to a culture medium, for the culture of the samples such as the above-stated microorganisms and cells. There are additives such as the pH indicator having characteristic optical absorption properties. Accordingly, there are cases when brightness or a way how it looks like of the sample to be observed may change resulting from the additive. It is possible to correspond to such a change when a visual observation by a person is performed because the brightness, contrast, and so on are appropriately adjusted by the person. However, there is a problem that it is impossible to distinguish whether various changes occurred on an image is resulting from the change of the sample or resulting from the additive, because the brightness and the contrast of a generated image may change when an automatic observation is performed by using an imaging apparatus such as a camera.

Propositions of an observation device and a wavelength limiting filter for the observation device according to the present application are to suppress a change of an image resulting from an additive, and to enable to generate an appropriate image in an automatic observation.

SUMMARY

An observation device of the present embodiment observing a sample cultured in a culture vessel includes an illuminating unit including an illumination optical system and illuminating the sample, an image-capturing unit including an imaging sensor and generating an image by capturing an image of the sample illuminated by the illuminating unit, and a wavelength limiting filter being placed on an optical axis of the illumination optical system and between the illuminating unit and the image-capturing unit, and limiting a part of wavelengths of an illumination light from the illumination optical system in accordance with optical absorption properties of an additive contained in a culture medium used for culturing the sample.

Preferably, the optical absorption properties of the additive may be at least one of an optical absorption property according to a pH change of the culture medium and an optical absorption property according to a concentration change of the culture medium.

Preferably, the wavelength limiting filter may limit a part of wavelengths of the illumination light in accordance with a sensitivity characteristic of the imaging sensor in addition to the optical absorption properties of the additive.

Preferably, a plurality of the wavelength limiting filters having different limiting wavelengths includes a plurality of the wavelength limiting filters having different limiting wavelength, and a filter controlling unit placing one of the wavelength limiting filters from among the plurality of the wavelength limiting filters on the optical axis of the illumination optical system and between the illuminating unit and the image-capturing unit in accordance with the optical absorption properties of the additive.

Preferably, the wavelength limiting filter is a filter of which limiting wavelengths are variable, and includes a limiting wavelength controlling unit changing the limiting wavelengths by the wavelength limiting filter in accordance with the optical absorption properties of the additive.

A wavelength limiting filter of the present embodiment for an observation device which includes an illuminating unit including an illumination optical system and illuminating the sample, an image-capturing unit including an imaging sensor and generating an image by capturing an image of the sample illuminated by the illuminating unit, and which observes the sample cultured in a culture vessel, in which the wavelength limiting filter is placed on an optical axis of the illumination optical system and between the illuminating unit and the image-capturing unit, and limits a part of wavelengths of an illumination light from the illumination optical system in accordance with optical absorption properties of an additive contained in a culture medium used for culturing the sample.

According to an observation device and a wavelength limiting filter for the observation device of the present invention, it is possible to suppress a change of an image resulting from an additive, and to enable to generate an appropriate image in an automatic observation.

DETAILED DESCRIPTION OF THE EMBODIMENTS

Hereinafter, embodiments of the present invention are described with reference to the drawings. Incidentally, in the present embodiments, it is described while using a phase-contrast microscope as an example of an observation device of the present invention.

Figure 1:
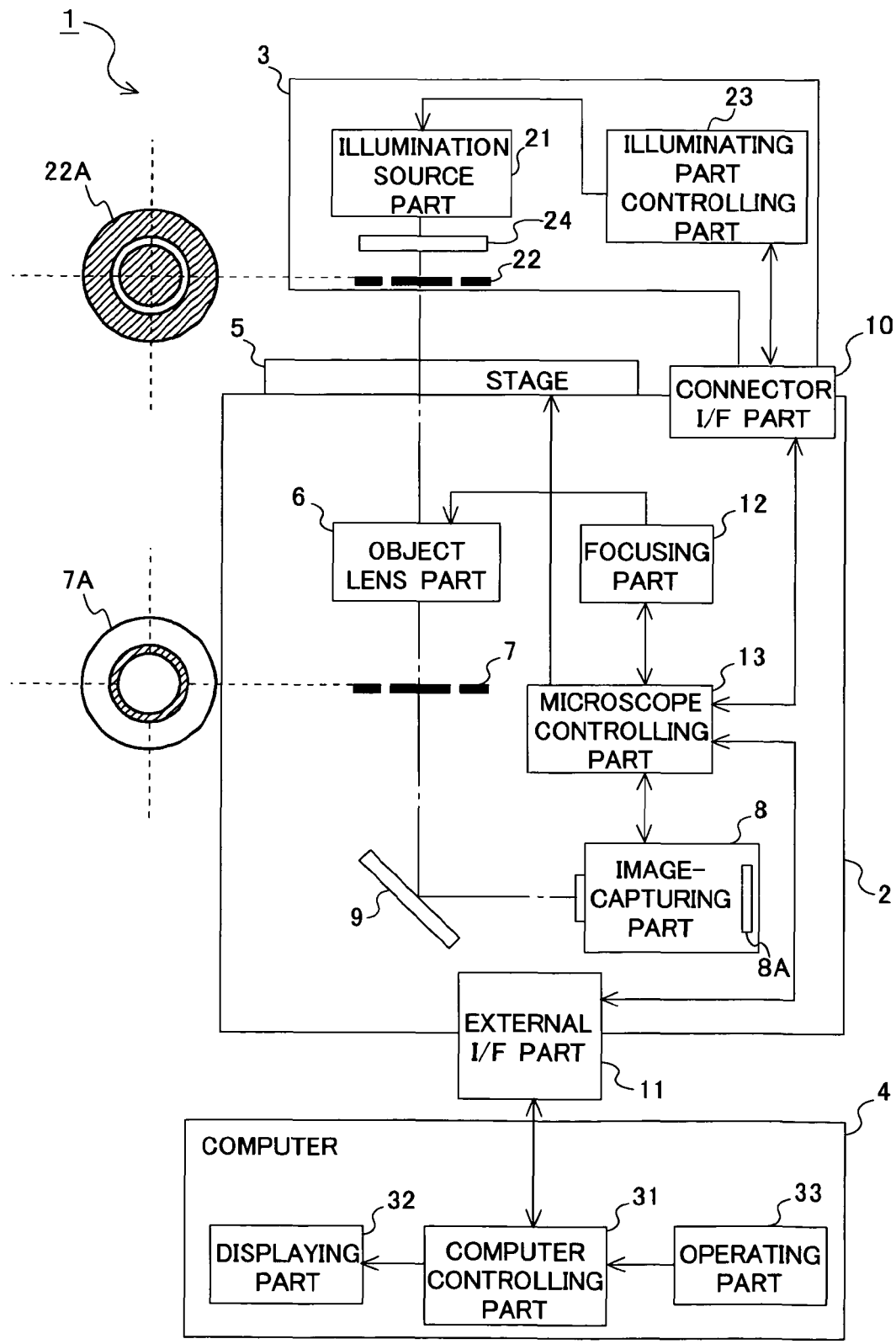
FIG. 1 is a block diagram illustrating a configuration of a microscope of the present embodiment.

FIG. 1 is a block diagram illustrating a configuration of a microscope in an embodiment of the present invention. As illustrated in FIG. 1, a microscope 1 is made up of a microscope body 2, an illuminating part 3 and a computer 4.

The microscope body 2 includes a stage 5 statically placing a sample being an observation object, an object lens part 6, a phase plate 7, an image-capturing part 8, and a mirror 9 guiding an optical flux from the object lens part 6 to the image-capturing part 8. Besides, the microscope body 2 includes a connector I/F part 10 which can be mutually coupled to the illuminating part 3, an external I/F part 11 which can be mutually coupled to the computer 4, a focusing part 12 performing focusing, and a microscope controlling part 13 controlling each part. The microscope controlling part 13 is mutually coupled to the image-capturing part 8, the connector I/F part 10, the external I/F part 11 and the focusing part 12, and controls the stage 5.

The object lens part 6 includes an object lens, an object lens driving part, an intermediate variable magnification part, and so on. Incidentally, it may have a constitution in which plural object lenses are included to be used by switching them. A sectional view of the phase plate 7 is designated with a reference numeral 7A. Besides, the image-capturing part 8 includes an imaging sensor 8A, an image processing part performing an image processing such as an A/D conversion, and so on.

The illuminating part 3 includes an illumination source part 21, a ring aperture 22, an illuminating part controlling part 23 controlling the illumination source part 21, and a wavelength limiting filter 24. The illumination source part 21 includes an illumination source such as an LED, a condenser lens, an aperture, a mirror, and so on. The illuminating part controlling part 23 is coupled to the microscope controlling part 13 via the above-stated connector I/F part 10, and controls the illumination source part 21 in accordance with an instruction of the microscope controlling part 13. A sectional view of the ring aperture 22 is designated with a reference numeral 22A.

The wavelength limiting filter 24 is a filter limiting a part of wavelengths of an illumination light from the illumination source part 21, and it is placed between the illumination source part 21 and the ring aperture 22 as illustrated in FIG. 1. A detail of the wavelength limiting filter 24 is described later.

The computer 4 includes a computer controlling part 31, a displaying part 32, an operating part 33, receives a user instruction relating to operations of the microscope 1 via the operating part 33, and displays an image acquired from the microscope 1 on the displaying part 32. Besides, the computer controlling part 31 records programs to control each part into a not-illustrated memory beforehand. The computer controlling part 31 is coupled to the microscope controlling part 13 via the external I/F part 11, acquires the image generated by the image-capturing part 8 from the microscope controlling part 13, and controls the microscope controlling part 13.

In an observation by the microscope 1, the illumination light is irradiated on a culture vessel statically placed on the stage 5 by the illumination source part 21. The illumination light is focused by the ring aperture 22, transmits through the wavelength limiting filter 24, and illuminates a sample inside the culture vessel on the stage 5. Optical flux transmitting through the sample (including direct light and diffracted light) transmits through object lens of the object lens part 6 and reaches the phase plate 7. The optical flux going through the phase plate 7 is guided to the image-capturing part 8 by the mirror 9. The image-capturing part 8 captures a transmitted image of the sample by the imaging sensor 8A to generate an image. The image generated by the image-capturing part 8 is an image having a contrast between light and dark caused by a phase difference.

The microscope controlling part 13 performs focusing by moving the stage 5 in a longitudinal direction to thereby change a surface to be an object of focusing, and by moving a part of the object lens part 6 in an optical axis direction of the object lens via the focusing part 12. Incidentally, the focusing is performed as same as the publicly known art, and therefore, the description thereof is not given.

Next, the wavelength limiting filter 24 is described. The wavelength limiting filter 24 is a filter limiting a part of wavelengths of the illumination light from the illumination source part 21 as stated above. Which part of the wavelengths is to be limited is determined by the additive contained in a culture medium used for the culture of the sample. Hereinafter, phenol red being a pH indicator is described as an example of the additive.

Figure 2:
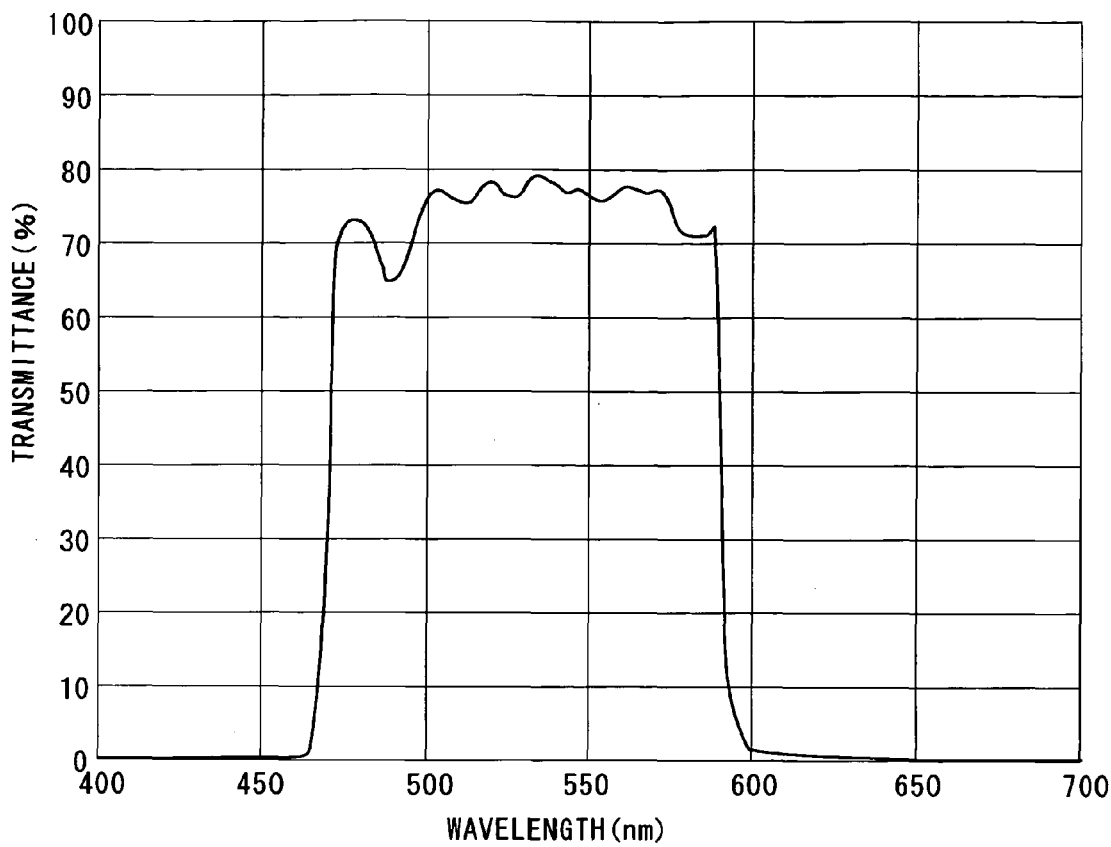
FIG. 2 is a view illustrating an optical absorption property of a GIF filter.

FIG. 2 is a view illustrating an optical absorption property of a GIF (green interference) filter generally used in a microscope. As illustrated in FIG. 2, transmittance of the GIF filter is high in a range of 500 nm to 600 nm, and an observation is performed by using the wavelengths within this area. Accordingly, it is easy to observe because it matches a visual range in a visual observation by a person.

Figure 3:
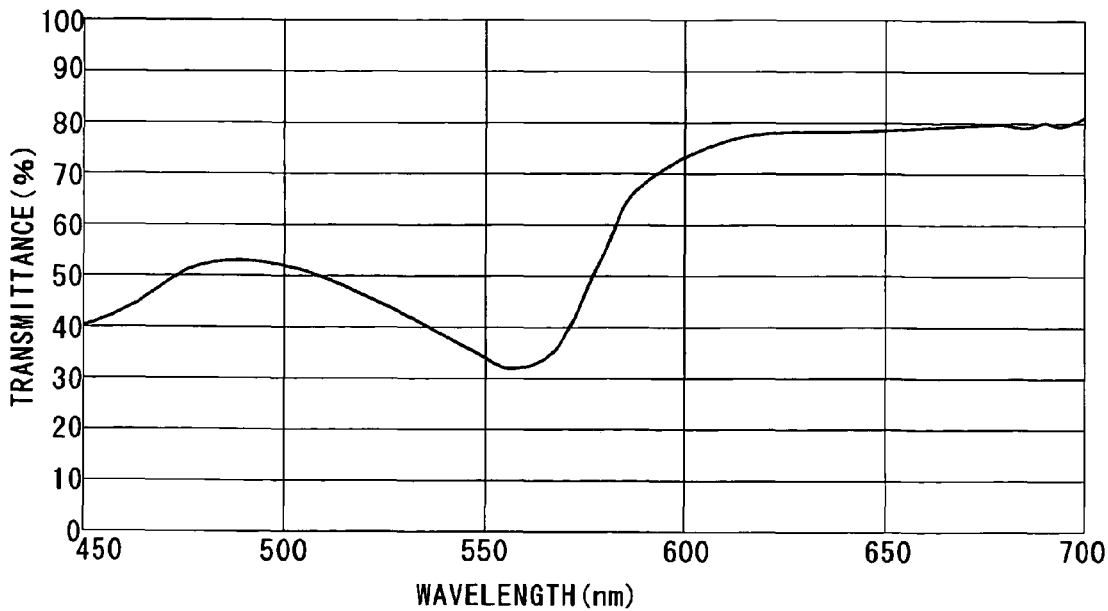
FIG. 3 is a view illustrating an optical absorption property of phenol red.

Next, the optical absorption property of phenol red is described. FIG. 3 is a view illustrating the optical absorption property of phenol red. As illustrated in FIG. 3, there is a characteristic absorption band in a vicinity of 500 nm to 600 nm in phenol red. This absorption band is known to change in accordance with a change of a pH value of the culture medium, thickness of the culture medium in the optical axis direction (hereinafter, it is called as "optical path length of culture medium"), and a concentration change of phenol red in the culture medium. Incidentally, the optical path length of the culture medium and the concentration change of phenol red in the culture medium are factors relating to the concentration of the culture medium.

Figure 4:
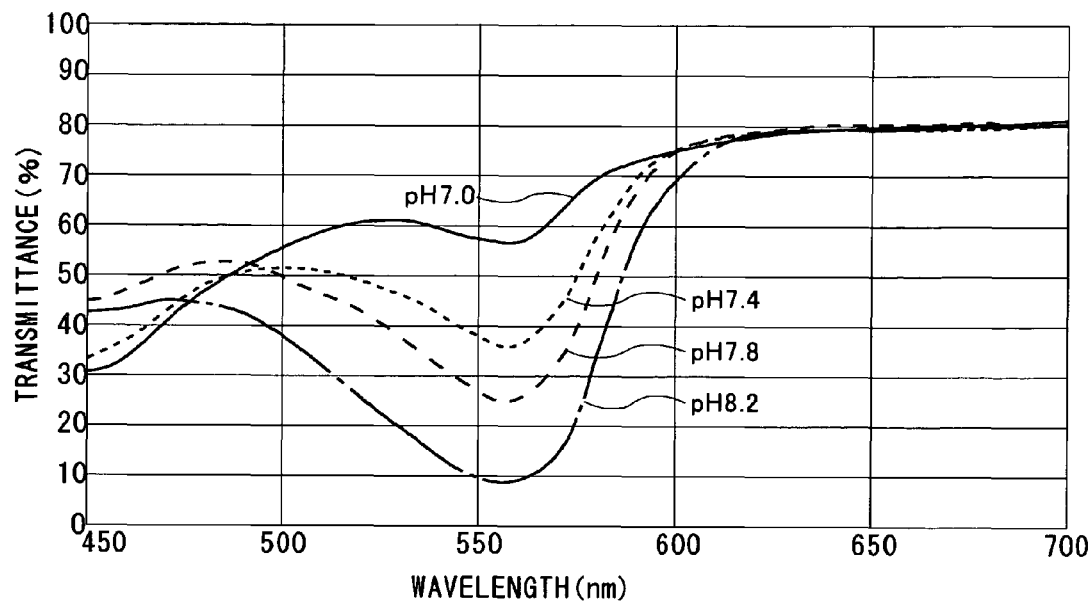
FIG. 4 is a view illustrating the optical absorption properties when an optical path length of a culture medium and a concentration of phenol red in the culture medium are fixed and a pH value of the culture medium is changed.

The optical absorption properties when the optical path length of the culture medium and the concentration of phenol red in the culture medium are fixed and the pH value of the culture medium is changed are illustrated in FIG. 4. As illustrated in FIG. 4, it can be seen that the changes of the optical absorption properties become large as the pH value becomes high such as pH 7.0, pH 7.4, pH 7.8, pH 8.2.

Figure 5:
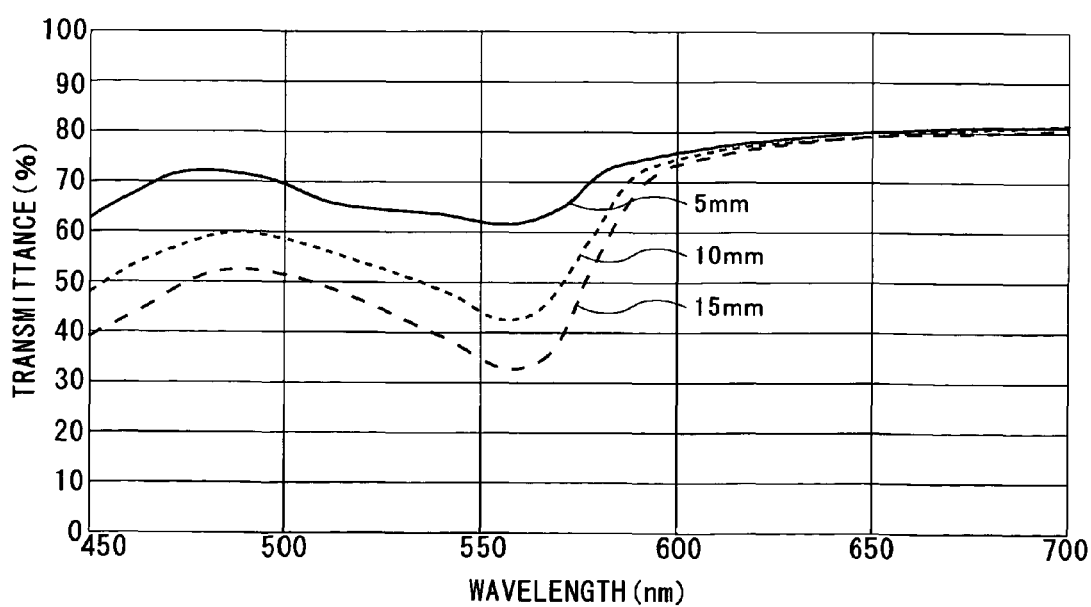
FIG. 5 is a view illustrating the optical absorption properties when the pH value of the culture medium and the concentration of phenol red in the culture medium are fixed and the optical path length of the culture medium is changed.

The optical absorption properties when the pH value of the culture medium and the concentration of phenol red in the culture medium are fixed and the optical path length of the culture medium is changed are illustrated in FIG. 5. As illustrated in FIG. 5, it can be seen that the changes of the optical absorption properties become large as the optical path length of the culture medium becomes long such as 5 mm, 10 mm, 15 mm.

The changes of the optical absorption properties become large as the concentration becomes high when the pH value of the culture medium and the optical path length of the culture medium are fixed and the concentration of phenol red in the culture medium is changed.

Figure 6:
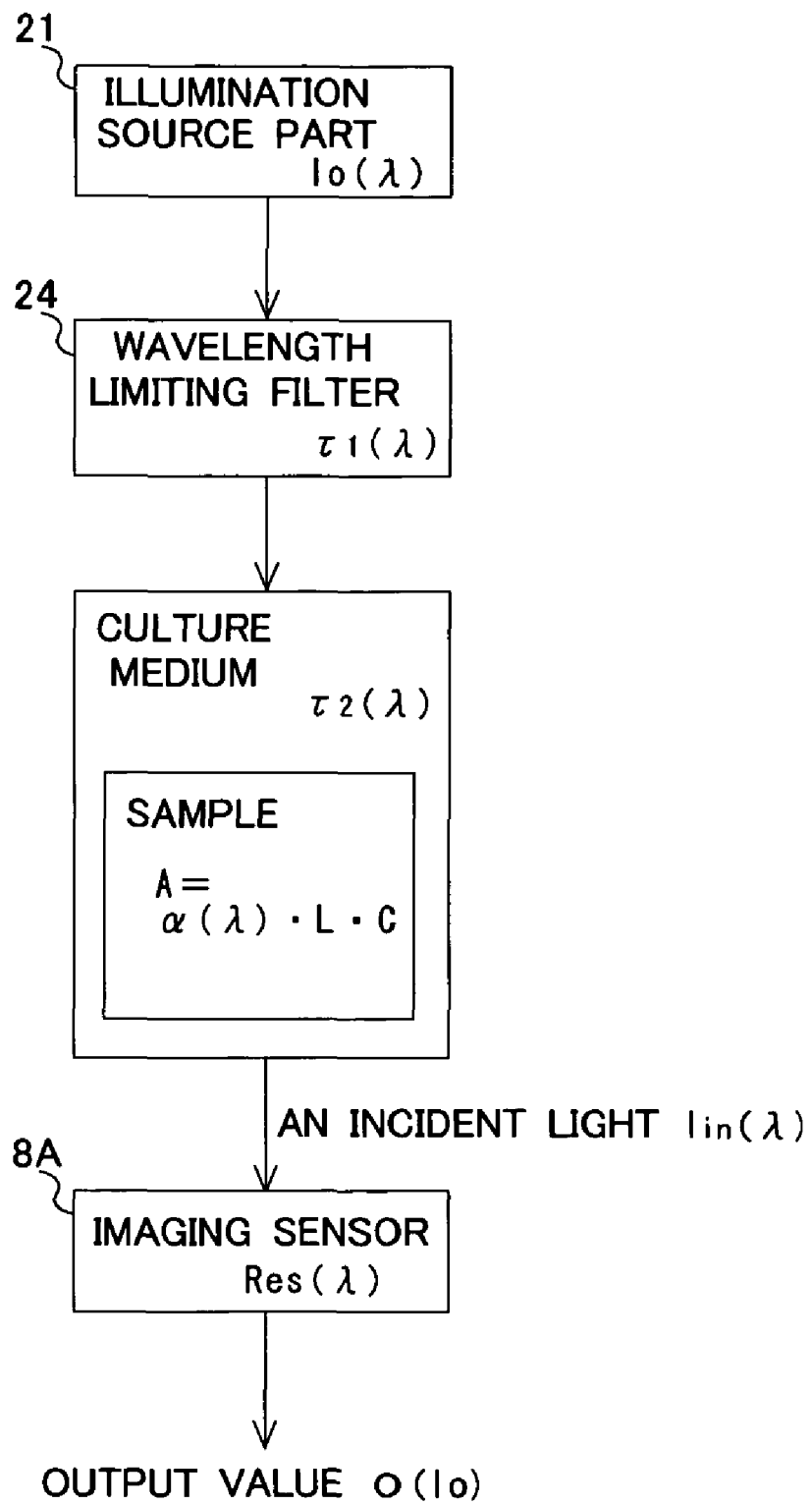
FIG. 6 is a view illustrating a flow until a light irradiated from an illumination source part 21 reaches an imaging sensor 8A, and an image is generated.

Here, a flow until the light irradiated from the illumination source part 21 reaches the imaging sensor 8A and the image is generated is considered. FIG. 6 is a view illustrating the flow until the light irradiated from the illumination source part 21 reaches the imaging sensor 8A and the image is generated. An incident light $I_{in}(\lambda)$ which is incident on the imaging sensor 8A in FIG. 6 is represented by the following expression 1.

$$I_{in}(\lambda) = I_o(\lambda) \times \tau_1(\lambda) \times \tau_2(\lambda) \times A \quad \text{(expression 1)}$$

Incidentally, in the expression 1, "$I_o(\lambda)$" represents an output of the illumination source part 21, "$\tau_1(\lambda)$" represents an influence of the wavelength limiting filter 24, "$\tau_2(\lambda)$" represents an influence of the culture medium (phenol red added to the culture medium), and "A" represents the optical absorption property resulting from surrounding media of the sample represented by the following expression 2.

$$A = \alpha(\lambda) \times L \times C \quad \text{(expression 2)}$$

Incidentally, "$\alpha(\lambda)$" represents an absorption constant, "L" represents the optical path length of the culture medium, and "C" represents the concentration of phenol red in the culture medium, in the expression 2.

Figure 7:
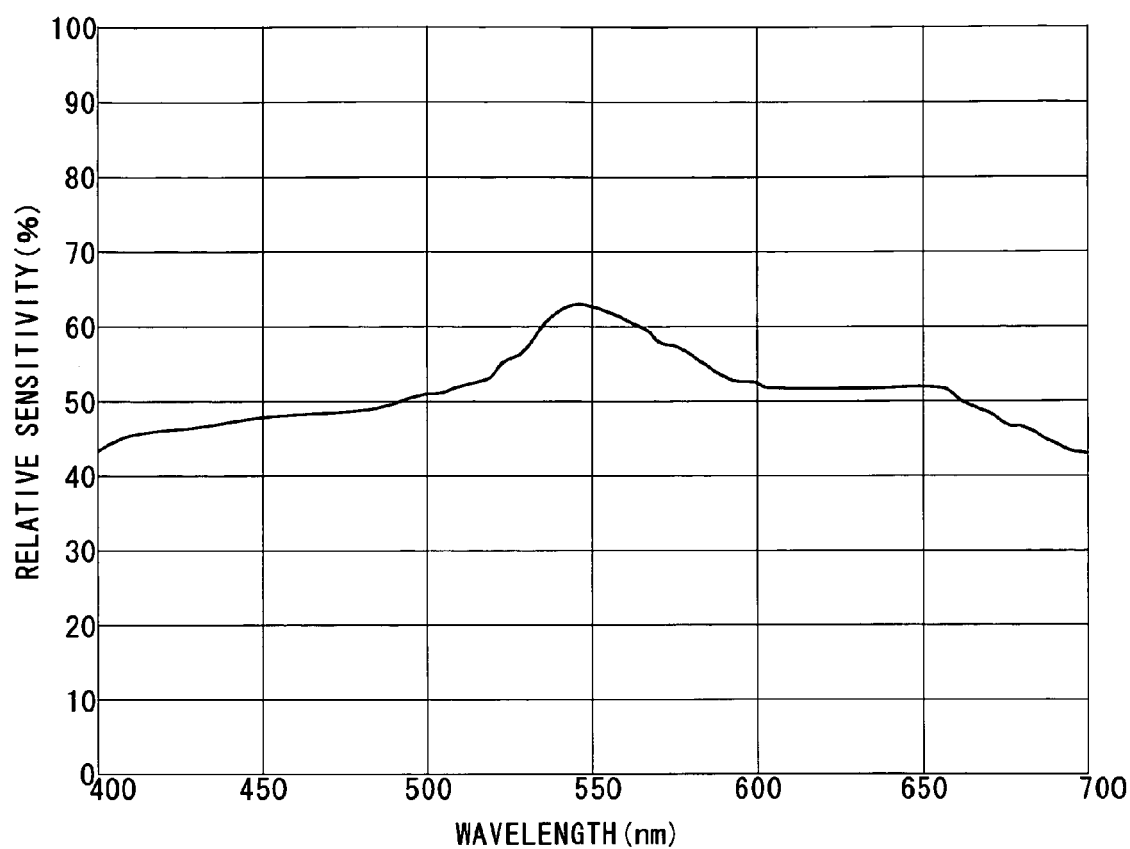
FIG. 7 is a view illustrating a spectral sensitivity characteristic of the imaging sensor 8A.

Besides, "$Res(\lambda)$" at the imaging sensor 8A in FIG. 6 represents a response function of the imaging sensor 8A. This response function is a function determined in accordance with a spectral sensitivity characteristic of the imaging sensor 8A. The spectral sensitivity characteristic of the imaging sensor 8A is illustrated in FIG. 7.

Next, an output value $O(I_o)$ when the image is generated by the imaging sensor 8A is described. Various wavelengths are combined in the generation of the image by the imaging sensor 8A, and the output value $O(I_o)$ is represented by the following expression 3.

$$O(Io) = \int_{\lambda min}^{\lambda max} Iin(\lambda) \cdot Res(\lambda) d\lambda \quad \text{(expression 3)}$$

As it is obvious from the expression 3, it is preferable that the wavelength limiting filter 24 is made up by considering a sensitivity characteristic of the imaging sensor 8A in addition to the optical absorption property of phenol red.

Figure 8:
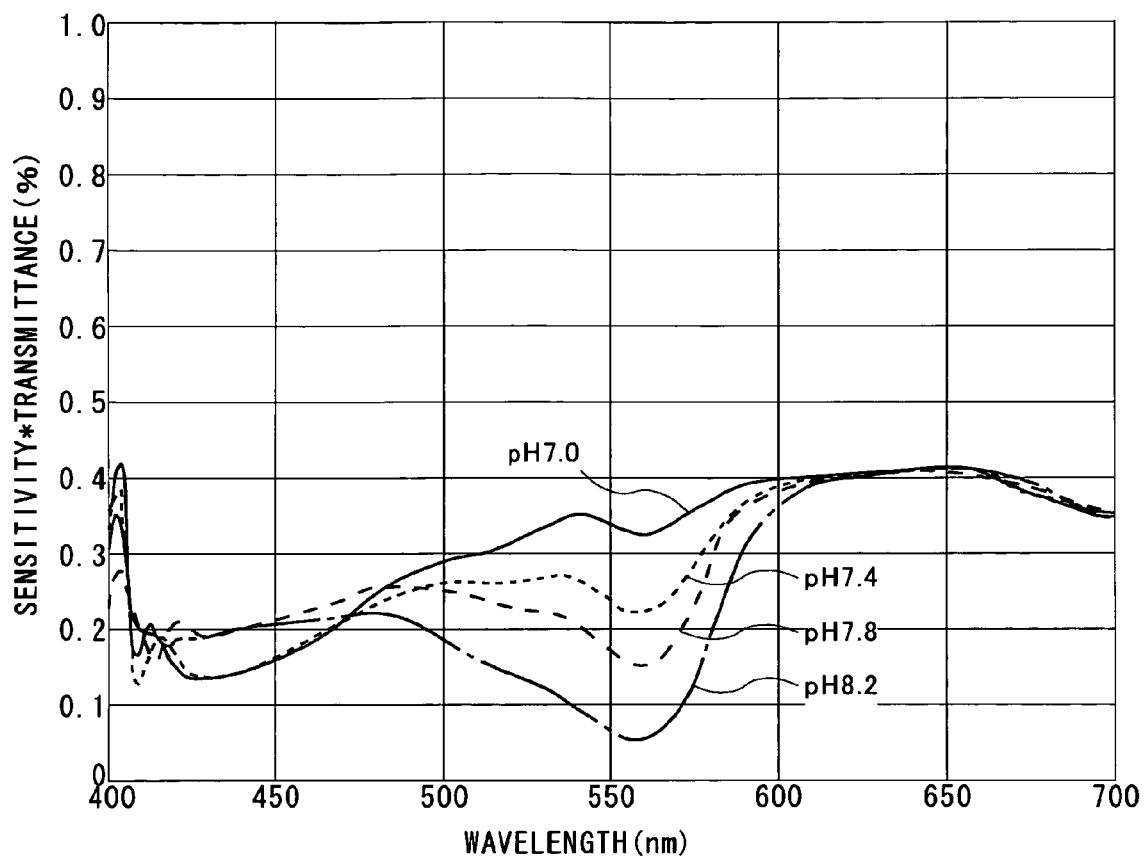
FIG. 8 is a view illustrating output characteristics when a sensitivity characteristic of the imaging sensor 8A is added to the optical absorption properties when the optical path length of the culture medium and the concentration of phenol red in the culture medium are fixed and the pH value of the culture medium is changed.

Accordingly, output characteristics when the sensitivity characteristic of the imaging sensor 8A is added to the optical absorption properties described in FIG. 4 when the optical path length of the culture medium and the concentration of phenol red in the culture medium are fixed and the pH value of the culture medium is changed are illustrated in FIG. 8. A vertical axis in FIG. 8 represents a change of a value in which the incident light $I_{in}(\lambda)$ incident on the imaging sensor 8A and the response function $Res(\lambda)$ of the imaging sensor 8A are multiplied and normalized into "0" (zero) to "1". As illustrated in FIG. 8, the output characteristics change largely within a range of 500 nm to 600 nm, and become stable within a range of 600 nm to 650 nm.

Figure 9:
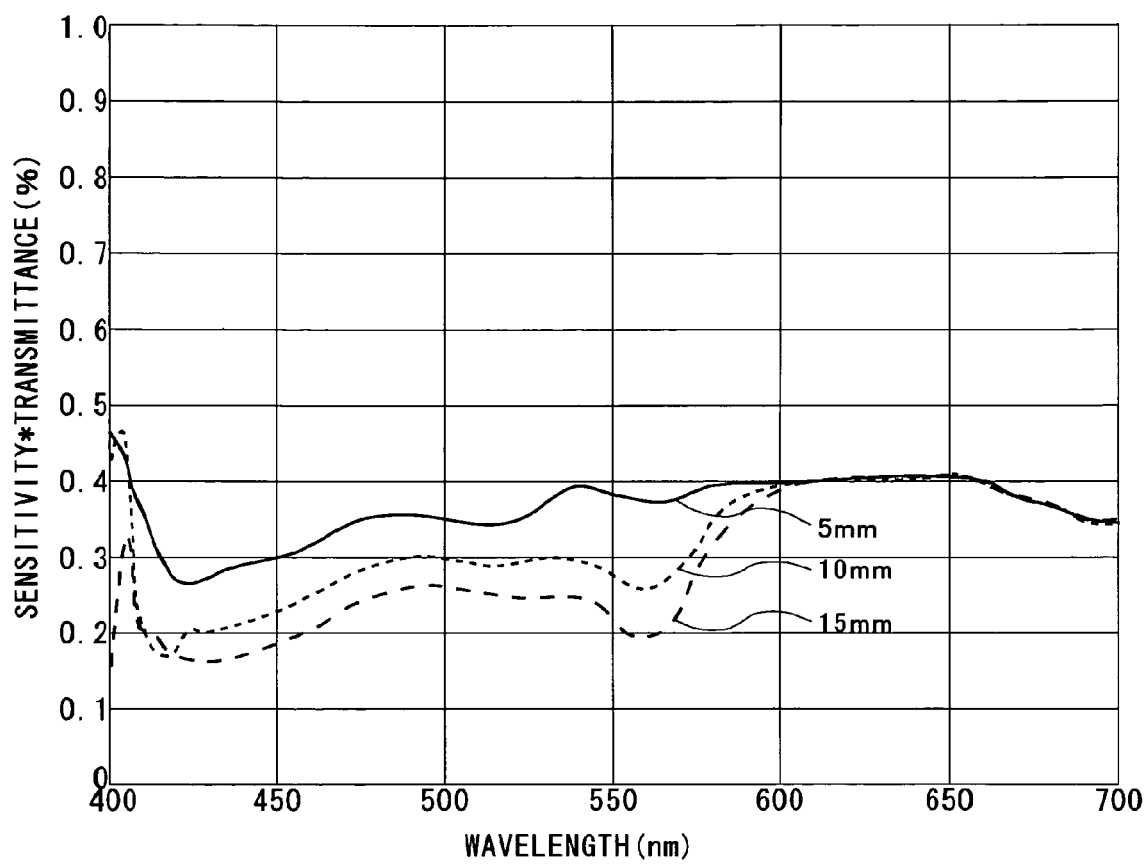
FIG. 9 is a view illustrating output characteristics when the sensitivity characteristic of the imaging sensor 8A is added to the optical absorption properties when the pH value of the culture medium and the concentration of phenol red in the culture medium are fixed and the optical path length of the culture medium is changed.

Besides, output characteristics when the sensitivity characteristic of the imaging sensor 8A is added to the optical absorption properties described in FIG. 5 when the pH value of the culture medium and the concentration of phenol red in the culture medium are fixed and the optical path length of the culture medium is changed are illustrated in FIG. 9. A vertical axis in FIG. 9 represents a change of a value in which the incident light $I_{in}(\lambda)$ incident on the imaging sensor 8A and the response function $Res(\lambda)$ of the imaging sensor 8A are multiplied and normalized into "0" (zero) to "1" as same as in FIG. 8. As illustrated in FIG. 9, the output characteristics change largely within a range of 500 nm to 600 nm, and becomes stable within a range of 600 nm to 650 nm.

The output characteristics similarly change largely within a range of 500 nm to 600 nm, and become stable within a range of 600 nm to 650 nm when the pH value of the culture medium and the optical path length of the culture medium are fixed and the concentration of phenol red in the culture medium is changed.

As it is described hereinabove, it is possible to obtain the stable output within the range of 600 nm to 650 nm even if the pH value of the culture medium to which phenol red is added is changed, the optical path length of the culture medium is changed, or the concentration of phenol red in the culture medium is changed. Further, the spectral sensitivity characteristic of the imaging sensor 8A becomes also stable within the range of 600 nm to 650 nm.

It is therefore possible to suppress the change of the image resulting from the addition of phenol red by generating the image while capturing the light with the wavelengths within the range of 600 nm to 650 nm in the imaging sensor 8A. Accordingly, the wavelength limiting filter 24 has a property transmitting the light with the wavelengths within the range of 600 nm to 650 nm, and limiting the light with the wavelengths other than the above. Incidentally, the detailed range of the limiting wavelengths may be determined in accordance with analysis accuracy of the image.

Figure 10:
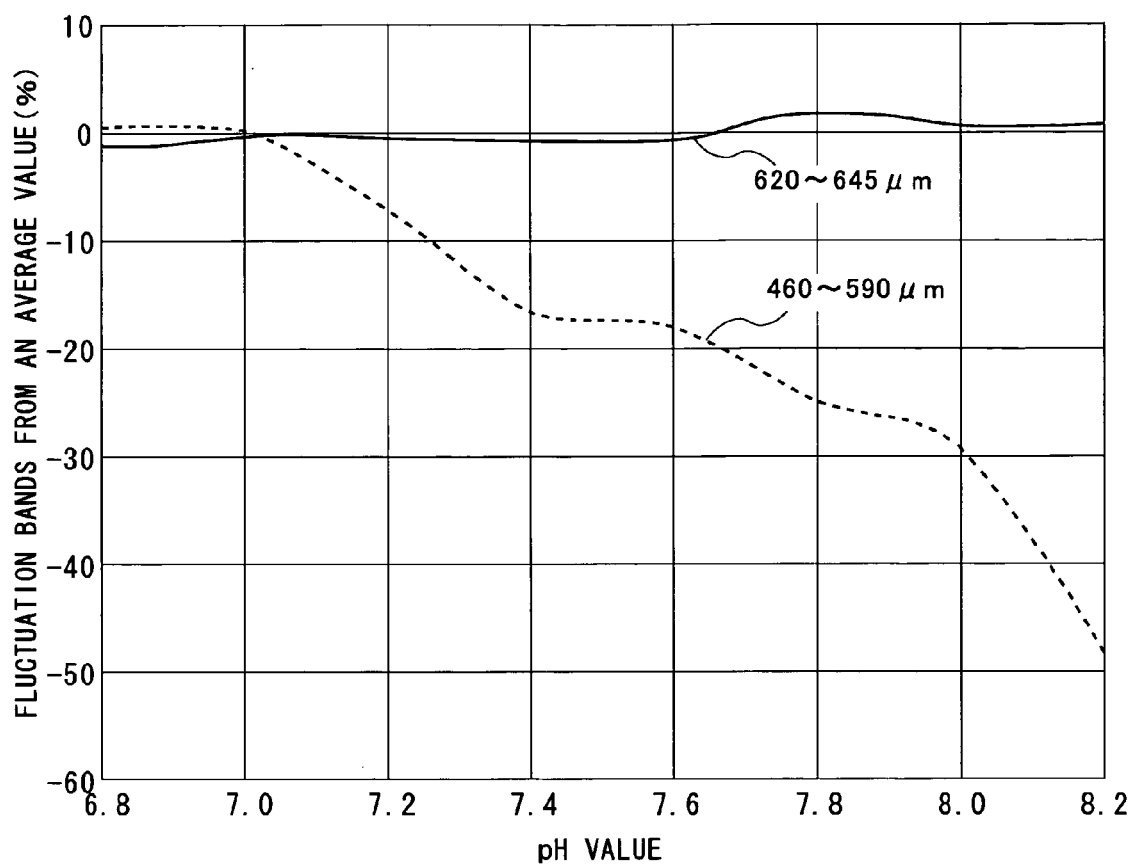
FIG. 10 is a view illustrating changes of fluctuation bands from an average value of an output value $O(I_o)$ according to the change of the pH value.

A graphic chart representing changes of fluctuation bands from an average value of the output value $O(I_o)$ according to the change of the pH value relating to two kinds of filters is illustrated in FIG. 10. One of the two kinds of filters is a filter such as the GIF filter having a high transmittance within a range of 460 nm to 590 nm, and the other is the wavelength limiting filter 24 of the present embodiment transmitting the light within a range of 620 nm to 645 nm. As it is obvious from FIG. 10, it is possible to obtain the stable output independent of the change of the pH value according to the wavelength limiting filter 24 of the present embodiment. Namely, the image of which change resulting from the addition of phenol red is small can be generated by the imaging sensor 8A.

Figure 11:
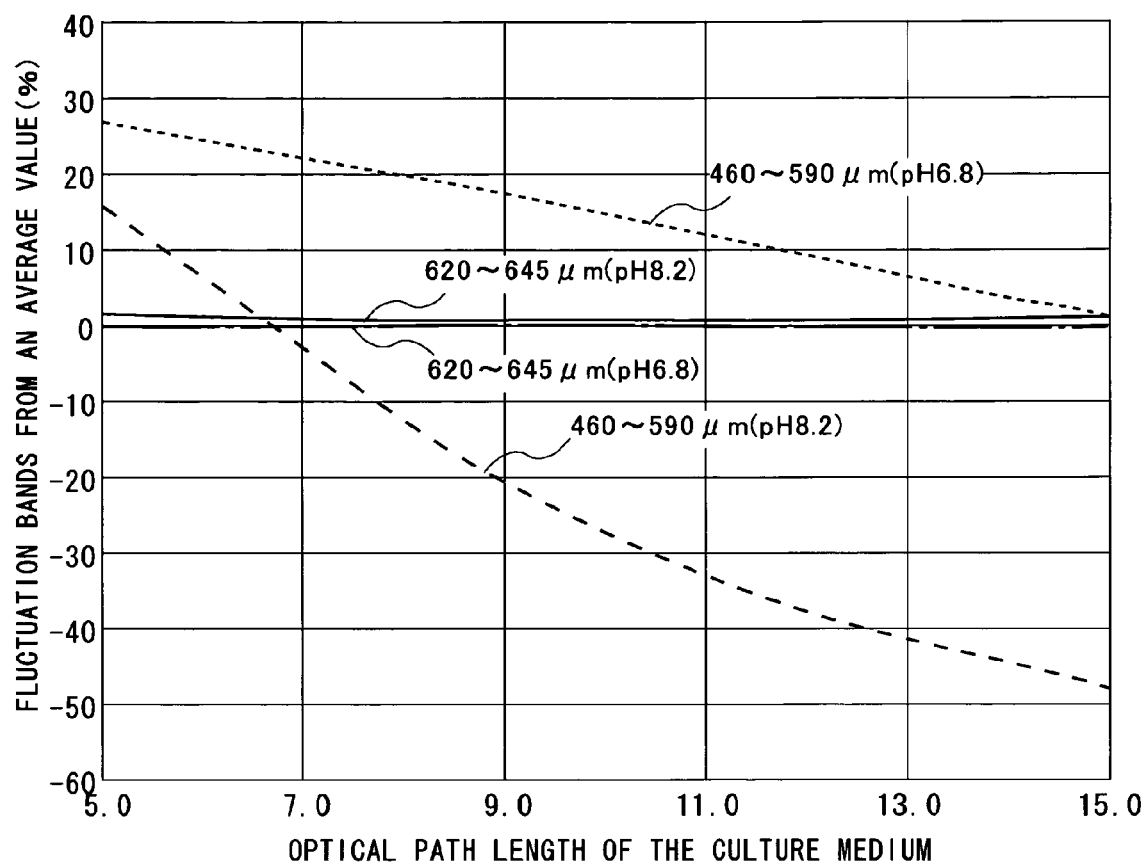
FIG. 11 is another view illustrating the changes of the fluctuation bands from the average value of the output value $O(I_o)$ according to the change of the pH value.

A graphic chart representing changes of fluctuation bands from an average value of the output value $O(I_o)$ according to the change of the optical path length of the culture medium relating to two kinds of filters as same as FIG. 10 is illustrated in FIG. 11. As it is obvious from FIG. 11, it is possible to obtain the stable output independent of the change of the optical path length of the culture medium according to the wavelength limiting filter 24 of the present embodiment. Namely, the image of which change resulting from the addition of phenol red is small can be generated by the imaging sensor 8A.

Incidentally, it is possible to obtain the stable output independent of the concentration change of phenol red in the culture medium according to the wavelength limiting filter 24 of the present embodiment.

Modification Example

Figure 12:
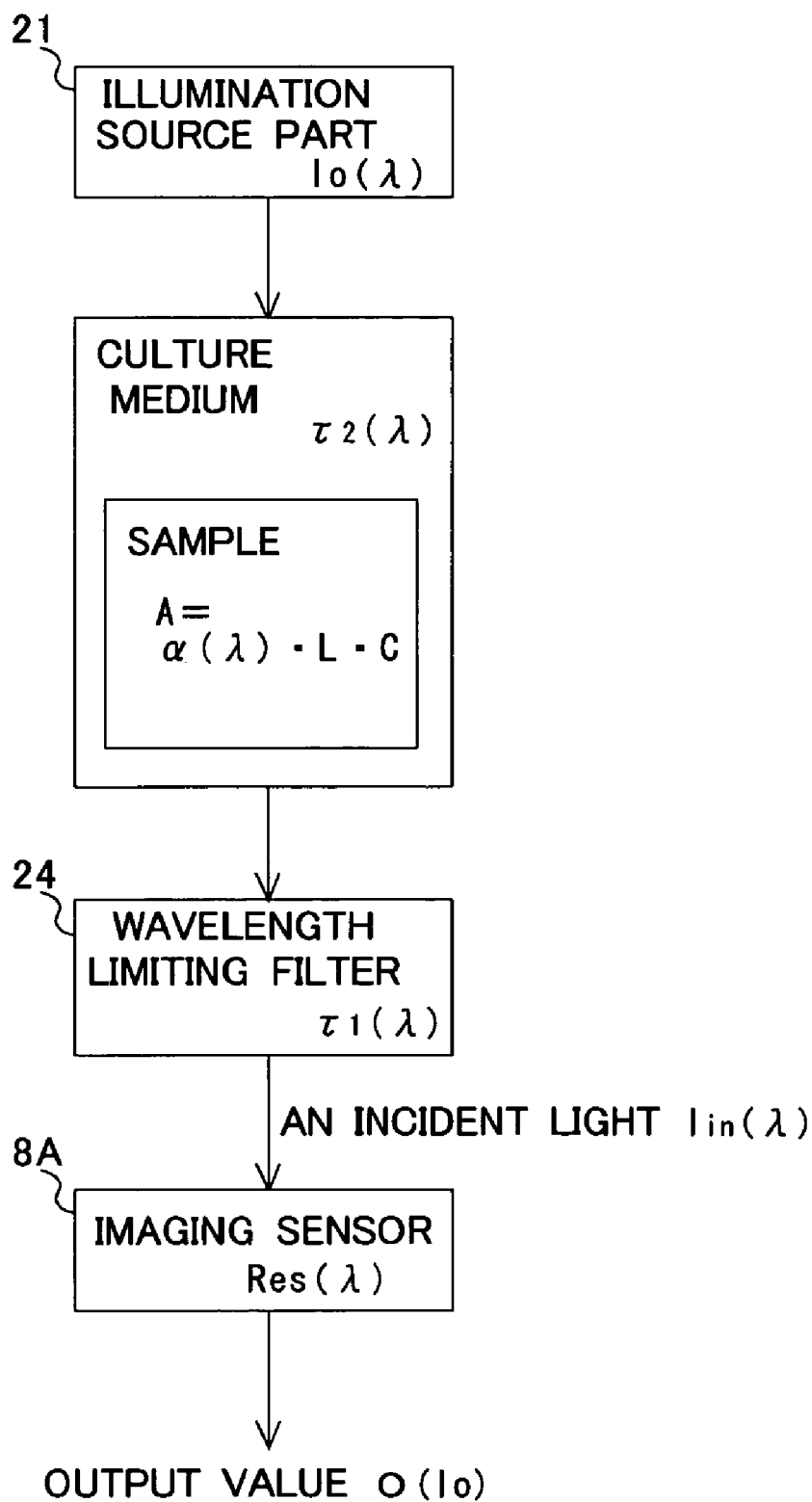
FIG. 12 is another view illustrating a flow until the light irradiated from the illumination source part 21 reaches the imaging sensor 8A, and an image is generated.

In the present embodiment, an example is illustrated in which the wavelength limiting filter 24 is placed between the illumination source part 21 and the ring aperture 22, but it may be placed at any position as long as it is between the illumination source part 21 and the image-capturing part 8 and on the optical axis of the illumination source part 21. A disposed position of the wavelength limiting filter 24 may be determined in accordance with the wavelengths limited by the wavelength limiting filter 24 and the constitution of the microscope 1. A flowchart until the light irradiated from the illumination source part 21 reaches the imaging sensor 8A and the image is generated when the wavelength limiting filter 24 is placed between the stage 5 and the image-capturing part 8 is illustrated in FIG. 12. As illustrated in FIG. 12, the incident light $I_{in}(\lambda)$ is similar to the case in FIG. 6 even though the position placing the wavelength limiting filter 24 is changed.

Besides, an example including a piece of wavelength limiting filter is described in the present embodiment, but it may have a constitution in which plural wavelength limiting filters having different limiting wavelengths are included, and any of the wavelength limiting filter from among the plural wavelength limiting filters is placed between the illumination source part 21 and the image-capturing part 8 in accordance with the optical absorption properties of the additive. For example, it may have a constitution in which the plural wavelength limiting filters having different limiting-wavelengths are provided at a turret and so on used for a fluorescence observation, and any of the wavelength limiting filters is placed between the illumination source part 21 and the image-capturing part 8.

Figure 13:
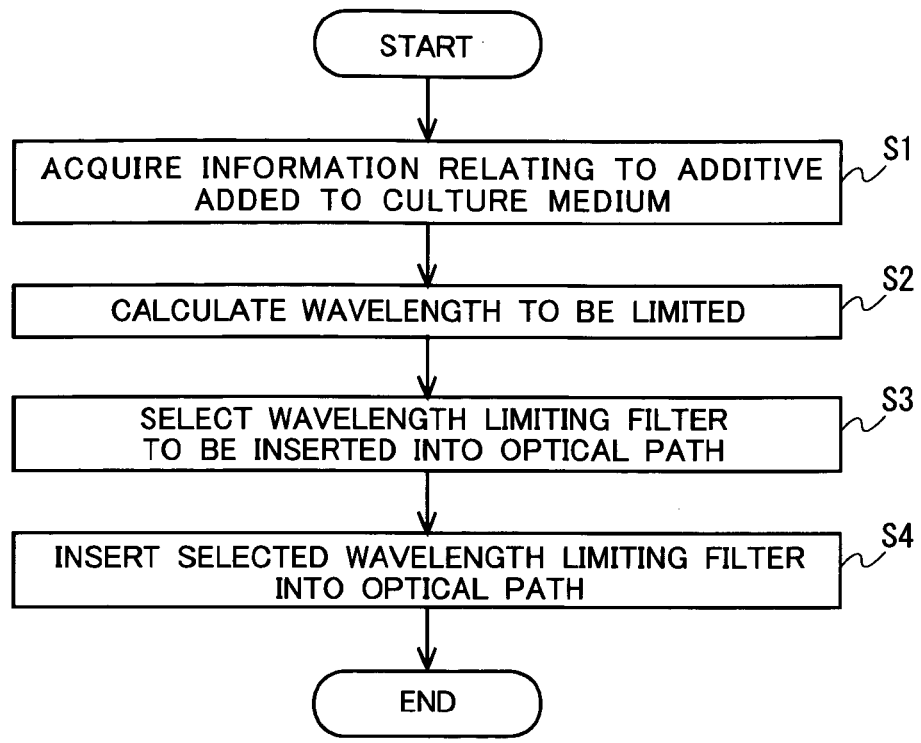
FIG. 13 is a flowchart illustrating operations of a computer controlling part 31.

A flowchart in FIG. 13 illustrates operations of the computer controlling part 31 when the plural wavelength limiting filters having different limiting wavelengths are included.

In step S1, the computer controlling part 31 acquires information relating to the additive added to the culture medium. The optical absorption property according to the pH change of the culture medium, the optical absorption property according to the concentration change of the culture medium, and so on are included in the information relating to the additive. Incidentally, the information relating to the additive used for the culture may be stored in advance, and only information relating to the kind and the concentration of the additive may be acquired.

In step S2, the computer controlling part 31 calculates the wavelengths to be limited. The computer controlling part 31 calculates the wavelengths to be limited based on the information acquired at the step SI as same as the method described in the above-stated embodiment.

In step S3, the computer controlling part 31 selects the wavelength limiting filter to be inserted into the optical path. The computer controlling part 31 selects the wavelength limiting filter to be inserted into the optical path from among the plural wavelength limiting filters in accordance with a calculation result in the step S2.

In step S4, the computer controlling part 31 inserts the selected wavelength limiting filter into the optical path. The computer controlling part 31 controls the microscope controlling part 13 via the external I/F part 11, and places the wavelength limiting filter selected at the step S3 at a predetermined position between the illumination source part 21 and the image-capturing part 8.

As stated above, it is possible to perform the observation by using an optimal wavelength limiting filter in accordance with the additive, if it has the constitution in which the plural wavelength limiting filters having different limiting wavelengths are included, and any of the wavelength limiting filter from among the plural wavelength limiting filters is placed between the illumination source part 21 and the image-capturing part 8 in accordance with the optical absorption properties of the additive. In particular, it is possible to perform the observation using the wavelength limiting filter described in the present embodiment without adding a new mechanism to the microscope if the turret and so on used for the fluorescence observation is used as stated above.

Besides, in the present embodiment, an example is described in which a piece of wavelength limiting filter is included, but it may have a constitution in which a modulation filter of which limiting wavelengths are variable is included, and the limiting wavelengths by the wavelength limiting filter are changed in accordance with the optical absorption properties of the additive.

Figure 14:
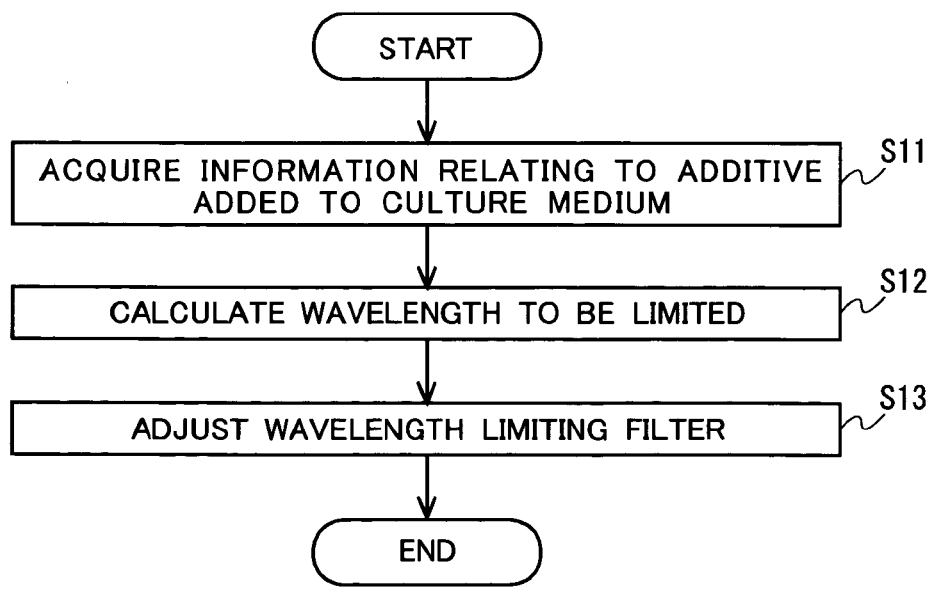
FIG. 14 is another flowchart illustrating the operations of the computer controlling part 31.

A flowchart in FIG. 14 illustrates operations of the computer controlling part 31 when the filter of which limiting wavelengths are variable is included.

In step S11, the computer controlling part 31 acquires information relating to the additive added to the culture medium. The optical absorption property according to the pH change of the culture medium, the optical absorption property according to the concentration change of the culture medium, and so on are included in the information relating to the additive. Incidentally, the information relating to the additive used for the culture may be stored in advance, and only information relating to the kind and the concentration of the additive may be acquired.

In step S12, the computer controlling part 31 calculates the wavelengths to be limited. The computer controlling part 31 calculates the wavelengths to be limited based on the information acquired at the step S11 as same as the method described in the above-stated embodiment.

In step S13, the computer controlling part 31 adjusts the wavelength limiting filter.

The computer controlling part 31 controls the microscope controlling part 13 via the external I/F part 11, and adjusts the wavelength limiting filter in accordance with a calculation result in the step S12.

As stated above, it is possible to perform the observation by optimizing the wavelength limiting filter in accordance with the additive, if it has the constitution in which the filter of which limiting wavelengths are variable is included, and the limiting wavelengths by the wavelength limiting filter is changed in accordance with the optical absorption properties of the additive.

Incidentally, it may have a constitution in which an imaging sensor in a spectral type is used as the imaging sensor 8A of the image-capturing part 8, and a light-receiving characteristic of the imaging sensor is changed in accordance with the calculation result in the step S12.

As it is described above, according to the present embodiment, an illuminating unit including an illumination optical system and illuminating a sample; an image-capturing unit including an imaging sensor and generating an image by capturing an image of the sample illuminated by the illuminating unit; and a wavelength limiting filter placed on an optical axis of the illumination optical system and between the illuminating unit and the image-capturing unit, and limiting a part of wavelengths of an illumination light from the illumination optical system in accordance with optical absorption properties of an additive contained in a culture medium used for a culture of the sample, are included. Accordingly, it is possible to suppress a change of the image resulting from the additive, and to enable to generate an appropriate image in an automatic observation. Besides, according to the present embodiment, it is possible to generate the image of which change of brightness is little, and therefore, shortening of time and accuracy improvement of focusing based on the image can also be expected.

According to the present embodiment, the optical absorption properties of the additive are the optical absorption property according to the pH change of the culture medium and the optical absorption property according to the concentration change of the culture medium. Accordingly, it is possible to generate the image of which change resulting from the addition of phenol red is small, even if the pH of the culture medium and the concentration of the culture medium are changed during the culture of the sample.

According to the present embodiment, the wavelength limiting filter limits a part of wavelengths of the illumination light in accordance with the sensitivity characteristic of the imaging sensor in addition to the optical absorption properties of the additive. Accordingly, it is possible to generate the image of which change resulting from the sensitivity characteristic of the imaging sensor is small.

Incidentally, in the present embodiment, phenol red being the pH indicator is described as an example of the additive, but the present invention can be similarly applied to the other pH indicators. It is also the same as for the additives other than the pH indicators. For example, it is possible to similarly apply the present invention to serum, various reagents, and so on being the additives added to the culture medium. In any case, the wavelengths limited by the wavelength limiting filter may be determined in accordance with the characteristics thereof as long as they are the additives having the change of the optical absorption property according to the pH change of the culture medium or the change of the optical absorption property according to the concentration change of the culture medium. For example, the optical absorption property of the serum changes according to the concentration change of the culture medium. Accordingly, the wavelengths limited by the wavelength limiting filter may be determined in accordance with the change of the optical absorption property according to the concentration change of the culture medium.

In the present embodiment, an example is described in which the wavelengths to be limited by the wavelength limiting filter are determined in accordance with the optical absorption property according to the pH change of the culture medium, the optical absorption property according to the concentration change of the culture medium, and the sensitivity characteristic of the imaging sensor. However, the wavelengths to be limited by the wavelength limiting filter may be determined in accordance with one or two elements from among the optical absorption property according to the pH change of the culture medium, the optical absorption property according to the concentration change of the culture medium, and the sensitivity characteristic of the imaging sensor.

In the present embodiment, the phase-contrast microscope is described as an example of a detection apparatus of the present application, but the present application can be similarly applied to the other microscopes and observation device.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. An observation device observing a sample cultured in a culture vessel, comprising:
   an illuminating unit including an illumination optical system and illuminating the sample;
   an image-capturing unit including an imaging sensor and generating an image by capturing an image of the sample illuminated by the illuminating unit; and
   a wavelength limiting filter being placed on an optical axis of the illumination optical system and between the illuminating unit and the image-capturing unit, and limiting a part of wavelengths of light entering the image-capturing unit by cutting off the part of wavelengths in accordance with optical absorption properties of an additive contained in a culture medium used for culturing the sample.

2. The observation device according to claim 1, wherein the optical absorption properties of the additive are at least one of an optical absorption property according to a pH change of the culture medium and an optical absorption property according to a concentration change of the culture medium.

3. The observation device according to claim 1, wherein the wavelength limiting filter limits a part of wavelengths of the light entering the image-capturing unit in accordance with a sensitivity characteristic of the imaging sensor in addition to the optical absorption properties of the additive.

4. The observation device according to claim 2, wherein the wavelength limiting filter limits a part of wavelengths of the light entering the image-capturing unit in accordance with a sensitivity characteristic of the imaging sensor in addition to the optical absorption properties of the additive.

5. The observation device according to claim 1, further comprising:
   a plurality of the wavelength limiting filters having different limiting wavelengths; and
   a filter controlling unit placing one of the wavelength limiting filters from among the plurality of the wavelength limiting filters on the optical axis of the illumination optical system and between the illuminating unit and the image-capturing unit in accordance with the optical absorption properties of the additive.

6. The observation device according to claim 2, further comprising:
   a plurality of the wavelength limiting filters having different limiting wavelengths; and
   a filter controlling unit placing one of the wavelength limiting filters from among the plurality of the wavelength limiting filters on the optical axis of the illumination optical system and between the illuminating unit and the image-capturing unit in accordance with the optical absorption properties of the additive.

7. The observation device according to claim 3, further comprising:
   a plurality of the wavelength limiting filters having different limiting wavelengths; and
   a filter controlling unit placing one of the wavelength limiting filters from among the plurality of the wavelength limiting filters on the optical axis of the illumination optical system and between the illuminating unit and the image-capturing unit in accordance with the optical absorption properties of the additive.

8. The observation device according to claim 1, wherein
   the wavelength limiting filter is a filter of which limiting wavelengths are variable, and
   the observation device comprises
   a limiting wavelength controlling unit changing the limiting wavelengths by the wavelength limiting filter in accordance with the optical absorption properties of the additive.

9. The observation device according to claim 2, wherein
   the wavelength limiting filter is a filter of which limiting wavelengths are variable, and
   the observation device comprises
   a limiting wavelength controlling unit changing the limiting wavelengths by the wavelength limiting filter in accordance with the optical absorption properties of the additive.

10. The observation device according to claim 3, wherein
    the wavelength limiting filter is a filter of which limiting wavelengths are variable, and
    the observation device comprises
    a limiting wavelength controlling unit changing the limiting wavelengths by the wavelength limiting filter in accordance with the optical absorption properties of the additive.

11. A wavelength limiting filter for an observation device which includes: an illuminating unit including an illumination optical system and illuminating a sample; and an image-capturing unit including an imaging sensor and generating an image by capturing an image of the sample illuminated by the illuminating unit, and which observes the sample cultured in a culture vessel, wherein
    the wavelength limiting filter is placed on an optical axis of the illumination optical system and between the illuminating unit and the image-capturing unit, and limits a part of wavelengths of light entering the image-capturing unit by cutting off the part of wavelengths in accordance with optical absorption properties of an additive contained in a culture medium used for culturing the sample.

\* \* \* \* \*